United States Patent

Balazs et al.

[11] Patent Number: 6,053,933
[45] Date of Patent: Apr. 25, 2000

[54] GRIPPING UNIT FOR APPLICATION IN MINIMALLY INVASIVE SURGERY

[75] Inventors: Matthias Balazs, Grafrath; Matthias Hähnle, München, both of Germany

[73] Assignee: Deutsches Zentrum für Luft- und Raumfahrt E.V., Bonn, Germany

[21] Appl. No.: 08/911,367

[22] Filed: Aug. 7, 1997

[30] Foreign Application Priority Data

Aug. 10, 1996 [DE] Germany ............... 196 32 298

[51] Int. Cl.⁷ ................................. A61B 17/28
[52] U.S. Cl. .......................... 606/205; 606/207
[58] Field of Search .................. 606/205–208, 606/210, 119

[56] References Cited

U.S. PATENT DOCUMENTS

| | | |
|---|---|---|
| 4,836,205 | 6/1989 | Barrett . |
| 4,890,615 | 1/1990 | Caspari et al. . |
| 5,217,460 | 6/1993 | Knoepfler . |
| 5,342,389 | 8/1994 | Haber et al. . |
| 5,507,774 | 4/1996 | Holmes et al. . |
| 5,569,299 | 10/1996 | Dill et al. ............................ 606/205 |
| 5,700,276 | 12/1997 | Benecke ............................... 606/206 |
| 5,713,919 | 2/1998 | Lahr ..................................... 606/205 |

FOREIGN PATENT DOCUMENTS

| | | |
|---|---|---|
| 3920706 | 1/1991 | Germany . |
| 9007356 | 5/1991 | Germany . |
| 4328855 | 1/1995 | Germany . |
| 4434938 | 2/1996 | Germany . |

OTHER PUBLICATIONS

"Suddeutsche Zeitung", KFW, Apr. 12, 1995.

*Primary Examiner*—Michael Buiz
*Assistant Examiner*—Kevin Truong
*Attorney, Agent, or Firm*—Browdy and Neimark

[57] ABSTRACT

A gripping unit for application in Minimally Invasive Surgery includes a stationary jaw (2) rigidly attached to a base section (4), a movable jaw (1) connected via a joint (5) to a push/pull rod (3), and an operating handle (6). The stationary jaw (2), the movable jaw (1), the push/pull rod (3) and the base section (4) have, in the longitudinal direction of the gripping unit, a channel (9) to receive an additional instrument (7), designed so that the channels (9, 30) in the base section (4) and in the push/pull rod (3) together form a circular conduit.

18 Claims, 7 Drawing Sheets

GRIPPING UNIT FOR APPLICATION IN MINIMALLY INVASIVE SURGERY

FIELD OF THE INVENTION

The invention pertains to a gripping unit for application in Minimally Invasive Surgery.

REVIEW OF THE RELATED TECHNOLOGY

Conventional gripping units used in Minimally Invasive Surgery, such as forceps or the like, are primarily intended for grasping, gripping or holding. They have a head part, essentially equipped with one movable and one stationary jaw or two movable jaws. Each movable jaw is operated by a push or pull rod, which is connected to the movable jaw via a joint.

The known gripping units furthermore have a tube-shaped shaft, encompassing, for example in the case of gripping units, the push or pull rods, respectively. In Minimally Invasive Surgery, gripping units are inserted into the body through small openings to the point where the surgical procedure is to be performed.

Gripping units furthermore have, at their proximal end outside the human body, a handle (part) used to operate the gripping unit, oftentimes (with handle openings) comparable, for example, to those of scissors, so that both pressure and a pulling movement can be exerted on the attached push or pull rod, respectively, via the handle part.

For the purposes of Minimally Invasive Surgery, the above-described gripping units for grasping, gripping or holding tissue parts, for example, have a diameter of 5 to 12 mm. The individual elements of a gripping unit may be connected with bolt joints, or the like. Gripping units of this type are known, for example, from DE 43 28 855 C1, DE 39 20 706 A1 and DE 90 07 356 U1. The movable jaws are operated via a push/pull rod which is connected to each movable jaw with a bolt. Each movable jaw is supported inside a stationary part of the gripping unit by a second bolt.

In gripping units used in Minimally Invasive Surgery, these types of joints have the disadvantage, on one hand, that gripping units of this type are difficult to sterilize because of the presence of edges, slits, gaps and overlapping surfaces; and, on the other hand, that it is impossible to place an additional instrument directly inside the gripping unit, primarily because of said joints and the like.

From DE 44 34 938 C1, a gripping unit is known in which the push/pull rod has a recess into which engages a pin of the movable jaw. The movable jaw, in turn, is supported via a pin inside the stationary part of the gripping unit. The transmission of force between the push/pull rod and the movable jaw takes place at a contact point of the pin in the recess of the push/pull rod. Since the pin performs a sliding motion inside the recess during opening and closing of the gripping unit, the lever arm of the force between the point where the force is applied and the pivot of the movable jaw is dependent on the opening angle of the gripping unit. This gripping unit has the particular disadvantage that it has not been possible to achieve a virtually constant coupling of force and distance.

Furthermore, a constant transmission of force over the entire range of motion of the jaws has not been implemented with the known gripping units. It is therefore not possible to obtain in the handle a largely undistorted image of the, operating forces.

The aim of the present invention is therefore to create a smooth-running gripping unit for application in Minimally Invasive Surgery, with which large forces can be precisely transmitted and which can furthermore be expanded with additional instruments.

To be able to expand a gripping unit by adding additional instruments such as an exploring probe or suction/irrigation devices, the gripping unit according to the invention, (which is preferably used in Minimally Invasive Surgery), has a channel, extending in a longitudinal direction and designed to receive at least one additional instrument, in a stationary jaw and in a base section which is rigidly connected to said stationary jaw.

In the conventional gripping units, a continuous channel cannot be formed because of the type of joints which have been used in the past. The movable jaw according to the invention, which may be connected to a push/pull rod via a bolt joint, for example, has therefore been designed with a groove located on opposite sides of the channel formed in the stationary jaw.

Since, in a connecting joint according to the invention, the joint is thus located in the outer area of the movable jaw. The push/pull rod is separated from the basis and can be moved relatively to it driving the movable jaw. A channel, into which additional instruments may be inserted, can thus be formed in the central area of the basis in a particularly advantageous manner. The inserted instrument can form the rigid jaw.

According to a further, preferred design of the invention, in addition to the stationary jaw and the base section rigidly connected to said jaw, the push/pull rod and optionally the movable jaw also have a channel extending in a longitudinal direction. In this case the channels are advantageously designed in the form of semi-circles, so that an assembled gripping unit has a conduit with a circular cross section formed by the two opposed channels.

This has the particular advantage that an inserted instrument can be rotated inside a conduit of this type with a circular cross-section, so that certain requirements can be performed. The inserted instrument preferably locks into place in angular positions of 0°, +/−45°, +/−90° and 180°, with the zero-degree-position being the position of an Instrument in which the top of the instrument, such as the sensor side of an exploring probe, is located opposite the movable jaw. This means that, for example, tissue may be grasped with the jaw of the instrument, and be examined with the inserted instrument.

If, for example, the exploring probe is rotated, preferably by 180°, from its initial position, either the tissue may be examined, for example, without having first been grasped, or the gripping unit according to the invention may be used as a conventional gripping unit, without requiring removal of the additional instrument from the gripping unit. In this case, the back of the instrument serves as the counterpart to the movable jaw. If the instrument is rotated by +/−45° from its starting position, the tissue which slides through the gripping unit, for example, can be continuously examined under light pressure.

In a further preferred design of the gripping unit according to the invention, the movable jaw protrudes over the stationary jaw in the longitudinal direction of the gripping unit, so that in the front part of the gripping unit only the probe, for example, is located opposite the movable jaw. In between the joint and the gripping unit (as segments of the movable jaw) there is a cavity to contain tissue while examining hard-to-reach areas, for example the backside of an intestine.

The above-described designs of the invention furthermore have the advantage that additional instruments may be exchanged inside the gripping unit, while the gripping unit is in use. A physician may thus, for example, insert successively different instruments into one and the same gripping unit in the course of a surgical procedure.

The gripping unit according to the invention can be separated into several modular components. These consist, for example, of an upper part and a lower part of the gripping unit, whereby the upper part may be the movable jaw and the push/pull rod, and the lower part may be the stationary jaw and the base section. This presents the particular advantage that the gripping unit according to the invention is easy to sterilize and can thus be used more than once. Undercuts, edges, slits, overlapping surfaces, and the like, have been eliminated as much as possible for an improved sterilization.

The individual modular components of the gripping unit are furthermore designed to be assembled without danger of confusion since an incorrect assembly is prevented by the unique joining geometries.

The gripping unit according to the invention is preferably made of corrosion-proof instrument steel, aluminum, POM (polyoxymethylene) or thermoplastics, such as PMMA or PTFE. The above materials may additionally have admixtures of short carbon fibers, fiber glass, contrasting agents or electrically conductive substances.

The invention also includes an improvement to an operating handle used in conventional gripping units, so that a physician or operator can guide the gripping unit with his little finger and ring finger, and partly with his thumb and ball of the thumb. The gripping function is carried out with the middle finger, so that the index finger remains freely movable and may be used, for example, to manipulate and to perceive the tactile signals of an actuator connected to the exploring probe.

The thumb is furthermore also used to rotate the instrument inserted into the gripping unit according to the invention. An actuator array, for example, may additionally be attached to the operating handle. The operating handle may have a serrated surface to lock the two jaws in various positions.

The gripping unit according to the invention furthermore operates with extremely low friction since the joint between the movable jaw and the push/pull rod is designed as a combination of a pin joint and two-piece coulisse. As a result, a rolling/sliding motion takes place along the contact surfaces of the coulisse. Since the lever arms of the joint remain virtually constant, this results in an even coupling of force and distance.

Furthermore, the radii of the coulisse are designed as large as possible to reduce the pressure and resulting wear and tear. The above-described design of the joint as a combination of a pin joint and coulisse makes it easy to disassemble the gripping unit according to the invention into its individual modular components: movable jaw-push/pull rod, stationary jaw-base section and operating handle. Additional parts consist of the inserted instrument and a guiding tube inside which the push/pull rod and base section are guided.

This design and the allocation of the various parts to the individual modules allows the operator to work with great precision.

BRIEF DESCRIPTION OF THE DRAWING

The above and other objects and the nature and advantages of the present invention will become more apparent From the following detailed description of an embodiment [s] taken in conjunction with drawings, wherein:

FIG. 5b is a side view of the distal end of the gripping unit corresponding to FIG. 5a, with an instrument in a position rotated by 180° from the preferred position presented in FIG. 5a;

FIG. 5c is a cross-sectional view along the line III—III of FIG. 5a;

DETAILED DESCRIPTION OF THE PREFERRED EMBODIMENT

Figure 1:
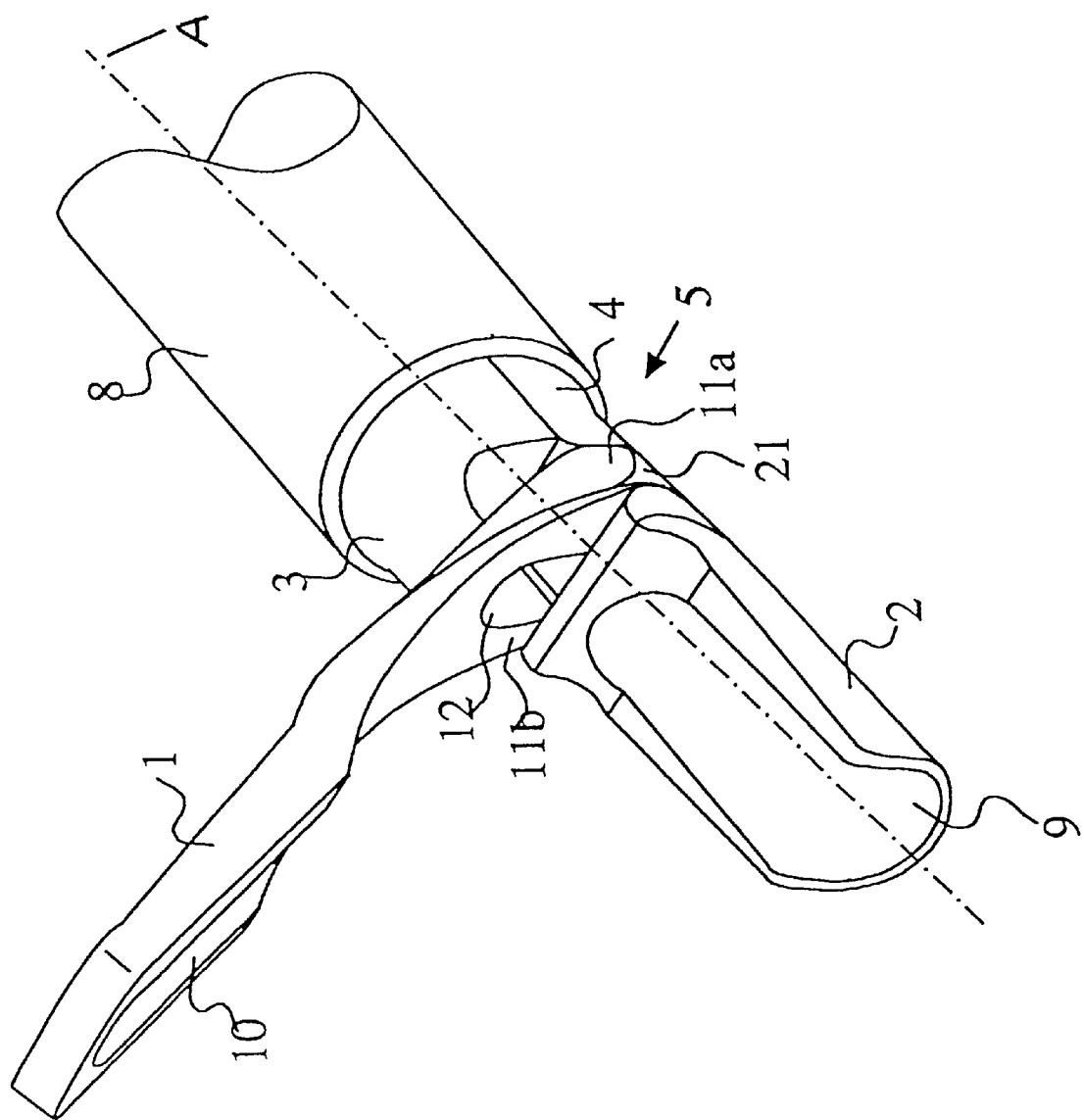
FIGS. 1 and 2 are schematic, perspective views of a preferred embodiment of the distal end of a gripping unit according to the invention in an opened and closed position, respectively.
Figure 2:
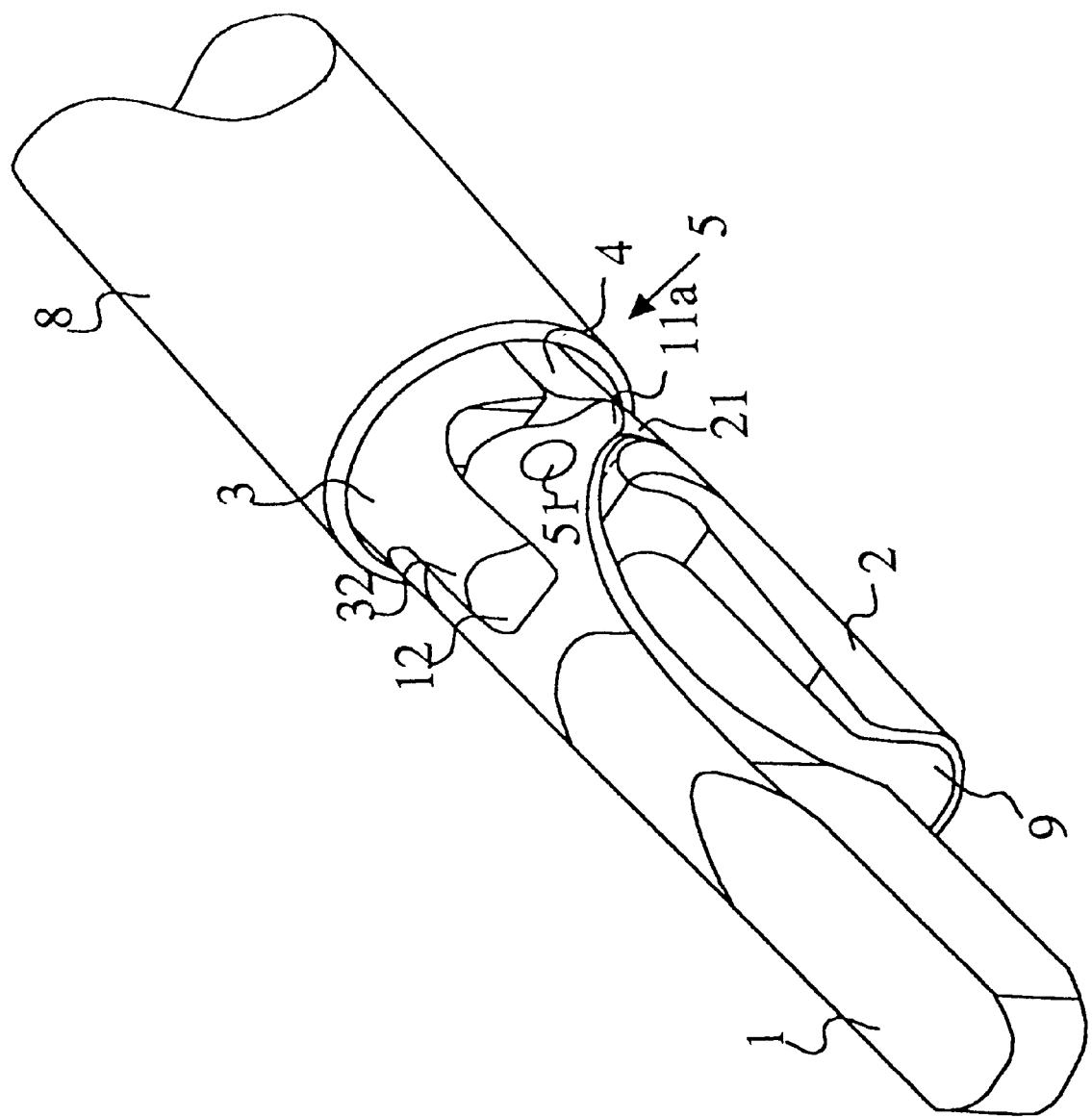

A preferred embodiment of a gripping unit according to the invention is described below, based on FIGS. 1 and 2, with FIG. 1 showing the gripping unit in an open position, and FIG. 2 showing the gripping unit in a closed position.

In FIGS. 1 and 2, a stationary jaw 2 is rigidly connected to a base section 4. A movable jaw 1 is connected to a push/pull rod 3 via a pin joint 51 which will be described in more detail later.

For this purpose, a projection 32 (FIG. 2) is formed at the front end of the push/pull rod 3, projecting into a recess 12 of the movable jaw 1. The movable jaw 1 has, on its end facing the push/pull rod 3, prolongations 11a and 11b—only the prolongation 11a of which is shown in the drawing—encompassing the recess 12. A pin 51 (see FIGS. 2, 5a and 5b) of the pin joint 5 forms a connection between the prolongations 11a and 11b of the movable jaw 1 and the projection 32 of the push/pull rod.

The prolongations 11a and 11b,respectively, of the movable jaw 1 protrude into a recess 21 which extends preferably perpendicular to the longitudinal axis or direction of the gripping unit—indicated by a dot-and-dash line A—and is formed in the transitional area between the stationary jaw 2 and the base section 4 which is rigidly connected to said stationary jaw. As shown in the side views in FIGS. 5a and 5b, the unattached end sections of the prolongations 11a and 11b of the movable jaw 1, which protrude into the recess 21, have an approximately semi-circular shape. As can also be seen particularly well from the side views in FIGS. 5a and 5b, the lower portion of the recess 21 has preferably a rhomboidic cross-section.

During opening and closing of the movable jaw 1 in relation to the stationary jaw 2, the prolongations 11a and 11b of the movable jaw 1 with their approximately semi-circular unattached ends, perform a sliding motion inside the recess 21 with its rhomboidic cross-section located between the stationary jaw 2 and the base section 4 which is rigidly attached to said stationary jaw 2. This results in the formation of a coulisse between the two jaws 1 and 2. The coulisse includes both prolongations 11a and 11b, and their respective recesses 21, best seen in FIGS. 5a and 5b, in which they slide and rotate. The push/pull rod 3 and the base tube 4 are furthermore housed and guided inside a tubular shaft 8 of the instrument.

As can be seen from the perspective view of the gripping unit in FIGS. 1 and 2, a channel 9 is formed in the lower jaw 2 of the gripping unit and in the base section which is rigidly connected to the jaw 2, whereby this channel 9 preferably has an approximately semi-circular cross-section. As can be seen from the perspective view in FIG. 1, a channel 10 is preferably also formed in the upper jaw 1, whereby the cross-section of said channel perpendicular to the longitudinal axis of the gripping unit—indicated by a dot-and-dash line—is preferably also semi-circular. The upper part of the push/pull rod 3 has a channel 30 matching the channel 10 in the movable jaw 1, whereby the channel 30 preferably also has a semi-circular cross section, as can be seen from the sectional view in FIG. 5c.

Figure 3:
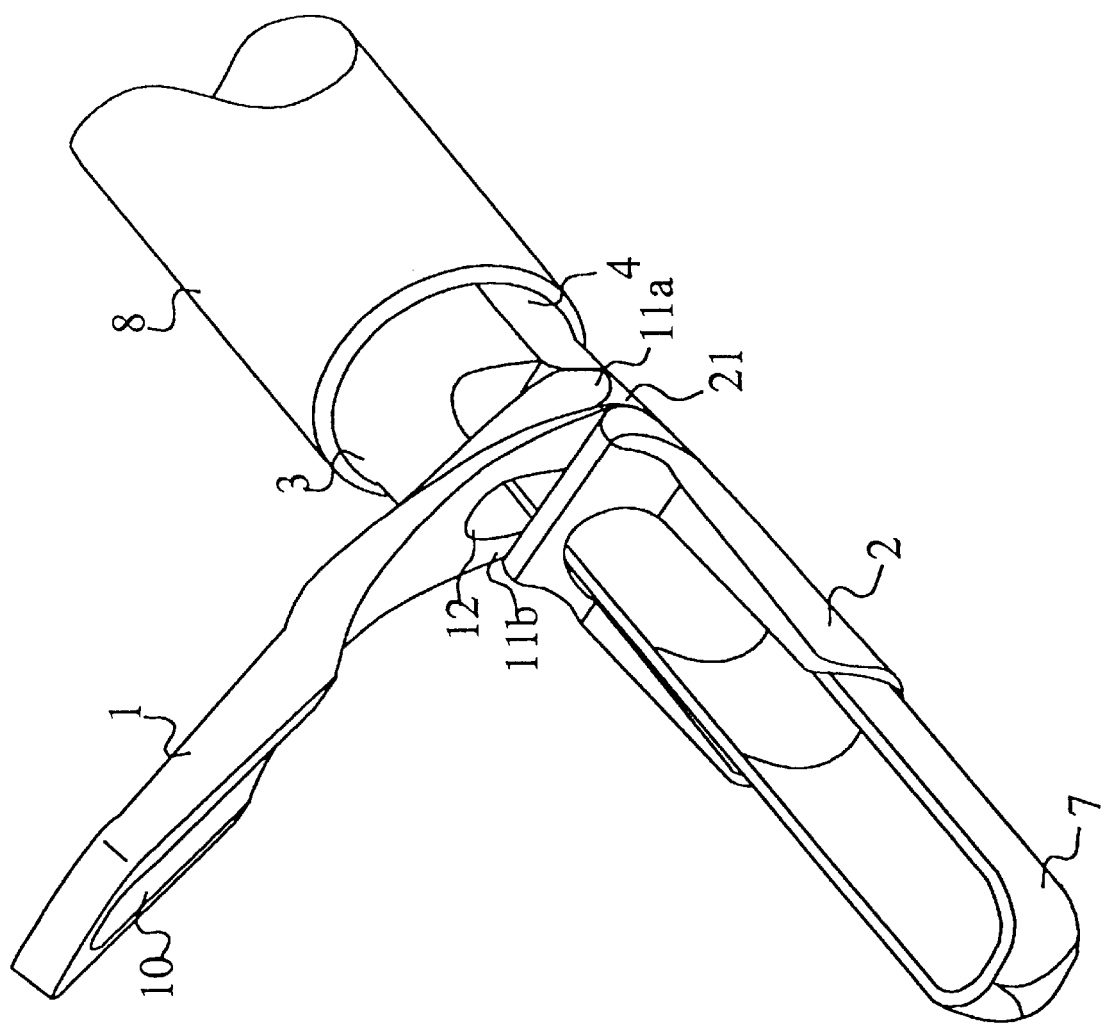
FIGS. 3 and 4 are schematic, perspective views of the preferred embodiment of the distal end of the gripping unit according to the invention corresponding to FIG. 1 and 2, with an instrument inserted.
Figure 4:
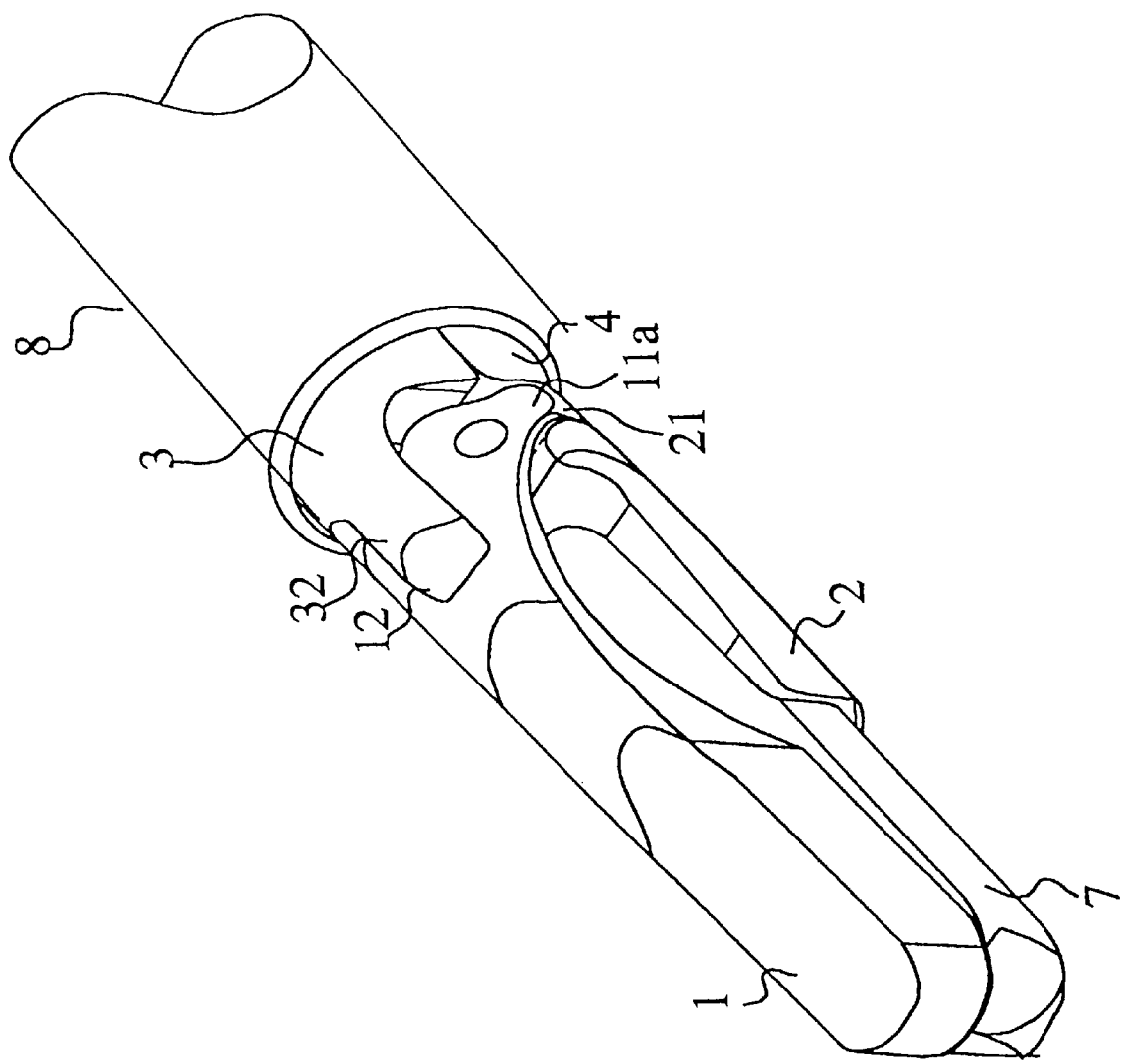

Regarding the gripping unit according to the invention, the drawings in FIGS. 3 and 4 correspond to those in FIGS. 1 and 2, respectively. However" in FIGS. 3 and 4, a schematically indicated instrument 7, for example in the form of an exploring probe, is shown inserted into the channel 9. The instrument 7 in the form of an exploring probe protrudes beyond the front end of the lower jaw 2 approximately so far that the unattached end of the instrument 7 does preferably not protrude beyond the front end of the movable jaw 1, as can be seen from FIG. 4.

In place of the instrument 7 in the form of an exploring probe, as shown in FIGS. 3 and 4, various other insertable instruments, which may be used to perform additional active and passive functions, may be inserted into the gripping unit according to the invention. The following may, for example, be inserted into the gripping unit in place of the exploring probe 7 shown in FIGS. 3 and 4: a suction and irrigation device, a laser, light conductors or optical fiber, or additional instruments used in Minimally Invasive Surgery, such as actively controlled optics, a miniature manipulator, or an insulated HF coagulation instrument, which may optionally even be designed in the form of a hook.

Figure 5A:
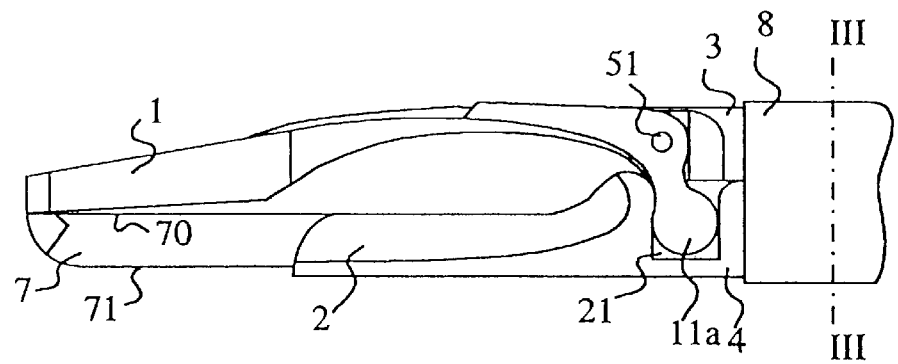
FIG. 5a is a side view of the distal end of the gripping unit presented in FIG. 4, with the inserted instrument in a starting position.

FIG. 5a shows the exploring probe in a starting position in which the sensing part 70 is facing the movable jaw 1. In the following, the starting position shown in FIG. 5a. to which the starting angle 0° has been assigned, will also be referred to as the preferred position.

In the course of a surgical procedure, the operator (surgeon) may, for example, use an operating handle, which will be described later based on FIG. 6, to pivot the-movable jaw 1 in the direction of the stationary jaw 2 and, in the process, press any tissue grasped in the course of the pivoting movement against the sensing surface 70 of the exploring probe 7.

Figure 5B:
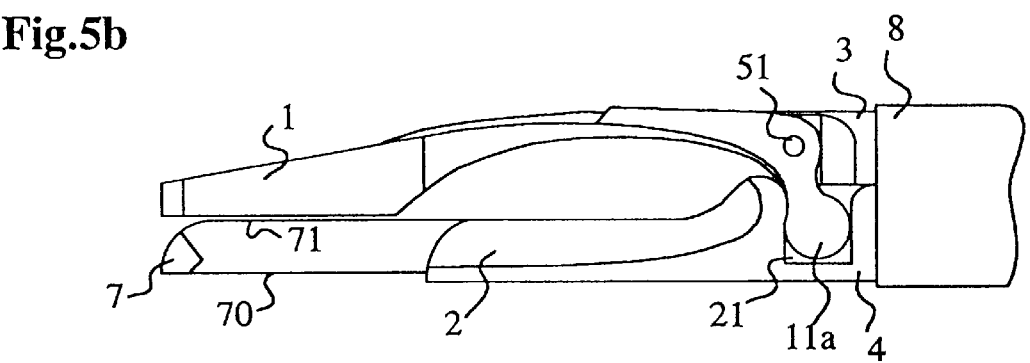

The presentation in FIG. 5b corresponds to that in FIG. 5a. as regards the gripping unit; only the exploring probe 7 is pivoted by 180° from the starting position shown in FIG. 5a. Due to the rotation by 180°, the sensing part 70 of the exploring probe 7 now faces downwards in FIG. 5b and no longer faces the movable jaw 1, as in FIG. 5a. In this position of the exploring probe, the gripping unit may be used to grasp tissue, for example, which in this position is being pressed against the back 71 of the probe 7. This may be advantageous if the objective is to only hold and not explore the tissue.

In the position of the probe 7 shown in FIG. 5b, in which the probe is turned by 180° from its initial position shown in FIG. 5a, the probe 7 may be used, for example, to explore hard-to-reach areas in which grasping of an object to be explored is not possible.

Figure 5C:
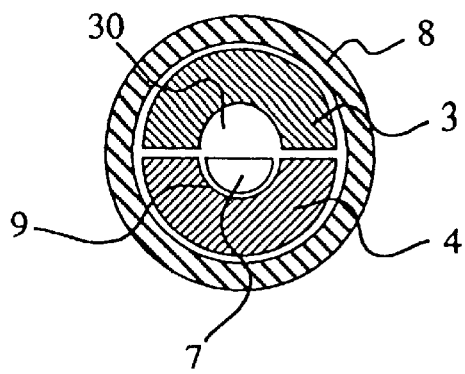

The section in FIG. 5c, along the line III—III of FIG. 5a, shows that the push/pull rod 3 also has an approximately semi-circular channel 30 opposite the channel 9 in the base section 4, The two opposed channels 9 and 30 in the base section 4 and in the push/pull rod 3, respectively, thus form an approximately circular conduit inside which an inserted instrument, such as an exploring probe, cannot only be turned by 180° around the longitudinal axis of the gripping unit indicated by a dash-and-dot line in FIG. 1, but in which the inserted instrument can also be moved into any random position between the positions presented in FIGS. 5a and 5b. This means that objects located to the side of the gripping unit can also be grasped in this manner. The inserted instrument 7 has a conical air tight housing 73 at its proximal end to contain the evaluation electronics for the sensor 70.

Figure 6:
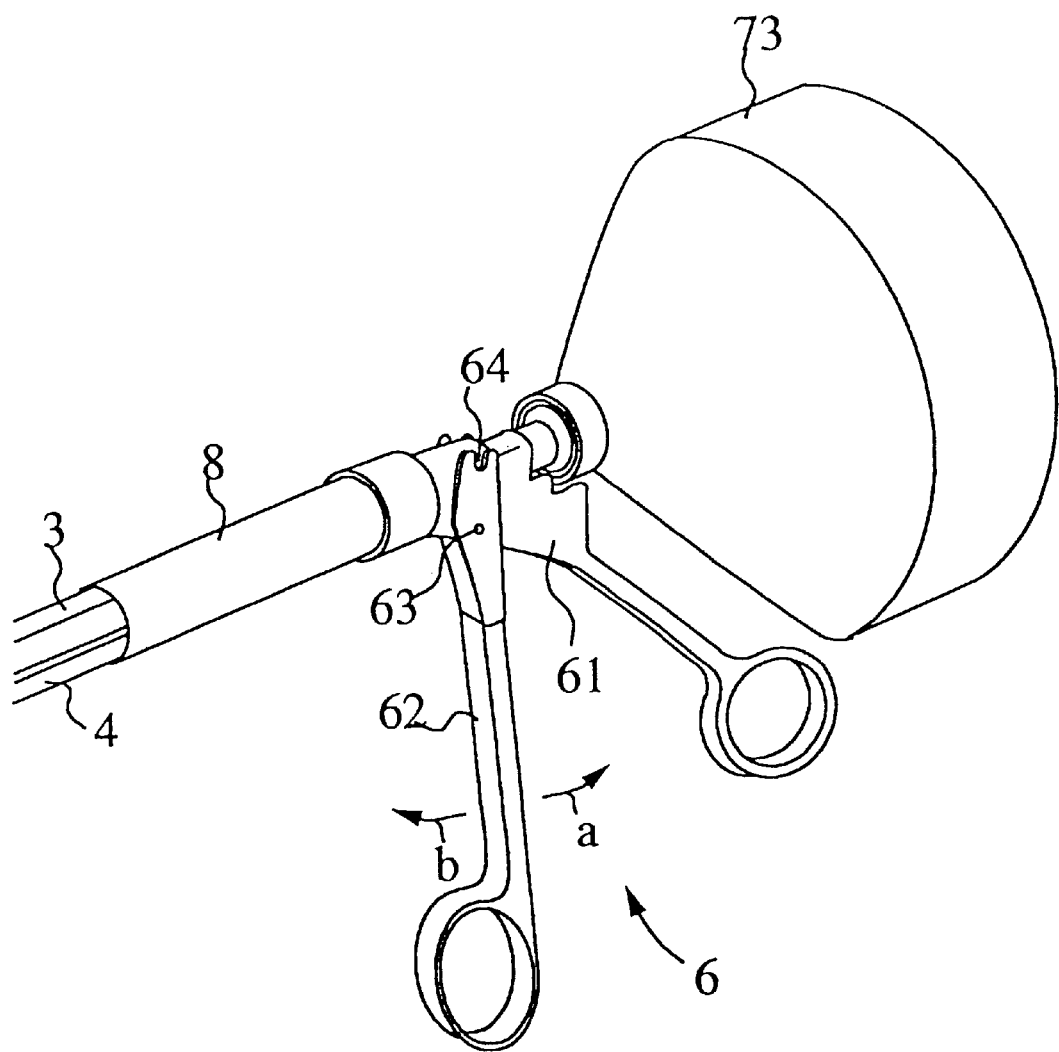
FIG. 6 is a perspective, schematic view of the proximal handle of the gripping unit according to the invention.

FIG. 6 shows the schematic perspective view of a preferred embodiment of an operating handle 6 of the gripping unit attached to the proximal end of the gripping unit. The operating handle 6 has a stationary handle part 61 which is rigidly connected to the base section 4. A second handle part 62 is used to move the push/pull rod 3 which is connected to the movable jaw 1, by pivoting the handle part 62 around a pin 63 in the direction of the arrows a or b.

If the handle part 62 is moved in the direction of the arrow a, i.e., towards the handle part 61, the push/pull rod 3 is moved to the left via a connecting part 64 in FIG. 6o and the movable jaw 1 is thus closed, i.e., moved into the position shown in FIGS. 2 and 4. If the handle part 62 is moved in the direction of the arrow b, the movable jaw 1 is opened in relation to the stationary jaw 2 and thus moved into a position shown in FIGS. 1 and 3.

The gripping unit furthermore has at its proximal end an insertion funnel 80 (not shown in detail) to facilitate the insertion, for example, of the exploring probe 7 or another instrument into the gripping unit during surgery.

The operating handle shown in FIG. 6 is a simplified design in which the design of an actuator array and a mechanism to rotate an instrument inserted into the gripping unit, for example, are not shown in detail.

Figure 7A:
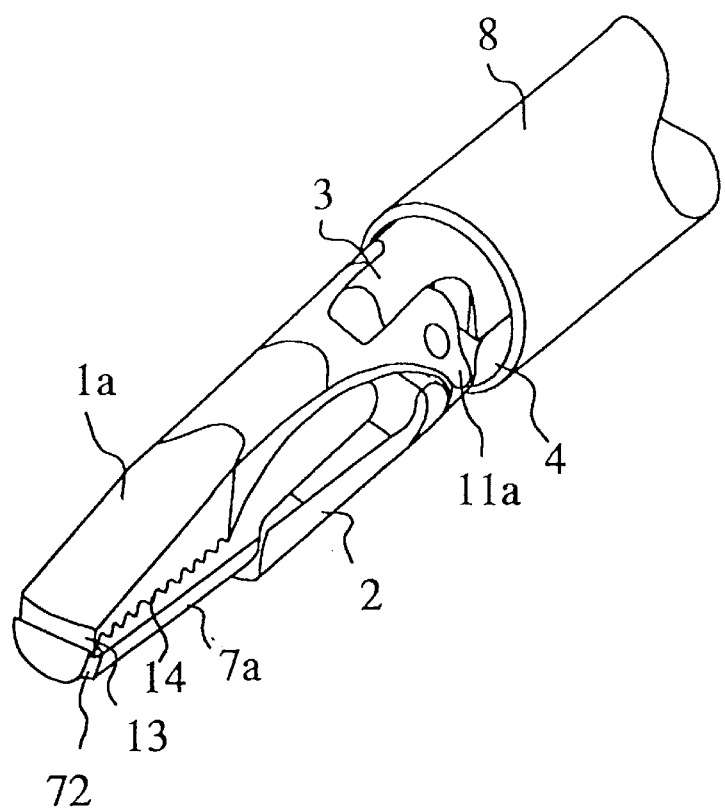
FIG. 7a is a schematic perspective view of the distal end of a further preferred embodiment of the gripping unit with a preferred embodiment of an inserted instrument in its starting position.
Figure 7B:
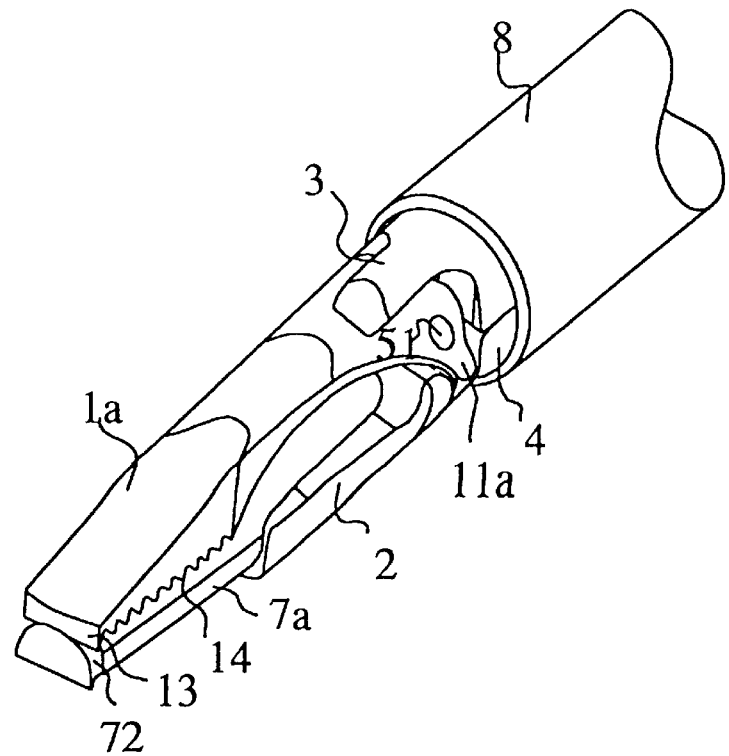
FIG. 7b is a perspective view corresponding to FIG. 7a, in which the instrument has been rotated by 180° from its starting position.

FIGS. 7a and 7b show the distal end of a gripping unit, the design of which corresponds to the gripping units described in FIGS. 1 through 5c, A movable jaw 1a is modified in this embodiment in so far as the movable jaw 1a has, at its distal end, a projection 13 pointing towards the stationary jaw 2 or an instrument 7a, respectively. When the gripping unit is closed, the projection 13 engages into a circumferential groove 72 of the instrument 7a. The gripping unit can thus perform a pointed grasping for a secure holding and vigorous Manipulation of the tissue, etc. grasped with the gripping unit. The side of the movable jaw 1a facing the Instrument 7a furthermore has a serrated surface 14 to further improve the handling of tissue, or the like.

The positions of the instrument 7a inside the gripping unit shown in FIGS. 7a and 7b correspond to the positions described based on the FIGS. 5a and 5b and the related advantageous handling possibilities.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means and Materials for carrying out various disclosed functions may take a variety of alternative forms without departing from the invention. Thus the expressions "means to . . . " and "means for . . . " as may be found in the specification above and/or in the claims below, followed by a functional statement, are intended to define and cover whatever structural, physical, chemical or electrical element or structure may now or in the future exist for carrying out the recited function, whether or not precisely equivalent to the embodiment or embodiments disclosed in the specification above; and it is intended that such expressions be given their broadest interpretation.

What is claimed is:

1. In a device for minimally invasive surgery, the device having an elongated shaft (8) defining a longitudinal direction and adapted to receive an optional additional instrument (7, 7a), an operating handle (6) at a first end of the shaft, and a gripping unit extending from a second end of the shaft; the improvement wherein the gripping unit comprises:

a base section (4) extending to the second end and terminating in a stationary jaw (2) rigidly attached thereto, the base section and the jaw comprising a first channel (9) extending in the longitudinal direction to receive the additional instrument (7, 7a) therein;

a push/pull rod (3) extending to the second end and connected to a movable jaw (1, 1a) via a pin joint (51) having a pin-joint axis; and a coulisse (11a, 11b, 21) coupling the movable jaw to the stationary law, whereby the movable jaw (1, 1a) is rotatable generally about a jaw axis of the movable law which is generally parallel to the pin-joint axis;

wherein the stationary law comprises a recess (21), the movable law comprises a pair of prolongations (11a, 11b), and the coulisse comprises the recess (21) and the pair of prolongations (11a, 11b) being rotatable fitted therein; and wherein the prolongations are formed on both sides of the first channel of the stationary law (2), whereby the channel is unobstructed;

whereby opening and closing of the movable jaw in relation to the stationary jaw is actuatable by a motion of the push/pull rod in the longitudinal direction.

2. The unit according to claim 1, wherein the movable jaw (1) includes a second channel (10).

3. The gripping unit according to claim 1, wherein the push/pull rod (3) includes a third channel (30) extending in the longitudinal direction.

4. The gripping unit according to claim 1, wherein the instrument (7, 7a) locks into place at preferred rotational angles 0°, +/–45°, and 180°.

5. The gripping unit according to claim 1, comprising means for the additional instrument (7, 7a) to be housed inside the gripping unit during a surgical procedure such that the instrument can be removed from or exchanged inside the gripping unit.

6. The gripping unit according to claim 1, wherein the gripping unit is disassembleable into modular components.

7. The gripping unit according to claim 6, wherein the modular components are assembleable without danger of confusion.

8. The gripping unit according to claim 1, wherein the gripping unit includes a material selected from the group consisting of corrosion-proof steel, aluminum, POM, thermoplastics, short carbon fiber, fiber glass, contrasting agents, electrically conductive substances, and combinations thereof.

9. The gripping unit according to claim 1, wherein the operating handle (6) includes an integrated actuator array.

10. The gripping unit according to claim 9, wherein the operating handle includes means for an index finger of an operator to remain freely movable during operation of the gripping unit to manipulate the actuator array.

11. The gripping unit according to claim 1, wherein the movable jaw (1a) includes at a distal end thereof, distal the second end, a projection (13) movable toward the additional instrument (7a) and engaging into a channel (72) of the additional instrument (7a) when the gripping unit is closed.

12. The gripping unit according to claim 1, comprising the additional instrument (7, 7a), and the operating handle (6).

13. The gripping unit according to claim 1, wherein the movable jaw (1, 1a) protrudes beyond the stationary jaw (2) in the longitudinal direction.

14. In a device for minimally invasive surgery, the device having an elongated shaft (8) defining a longitudinal direction and adapted to receive an optional additional instrument (7, 7a), an operating handle (6) at a first end of the shaft, and a gripping unit extending from a second end of the shaft; the improvement wherein the gripping unit comprises:

a base section (4) extending to the second end and terminating in a stationary law (2) rigidly attached thereto, the base section and the law comprising a first channel (9) extending in the longitudinal direction to receive the additional instrument (7, 7a) therein;

a push/pull rod (3) extending to the second end and connected to a movable law (1, 1a) via a pin joint (51) having a pin-loint axis; and a coulisse (11a, 11b, 21) coupling the movable law to the stationary law, whereby the movable law (1, 1a) is rotatable generally about a law axis of the movable law which is generally Parallel to the pin-joint axis, whereby opening and closing of the movable law in relation to the stationary law is actuatable by a motion of the push/pull rod in the longitudinal direction;

wherein the stationary jaw comprises a recess (21), the movable jaw comprises a prolongation (11a, 11b), and the coulisse comprises the recess (21) and the prolongation (11a, 11b) being rotatably fitted therein; and wherein the recess is offset from the pin joint in a direction transverse to the longitudinal direction and the pin-joint axis.

15. The gripping unit according to claim 14, wherein a rolling/sliding motion takes place along contact surfaces of the prolongation and the recess upon a rotation of the coulisse, and wherein the sliding motion is transverse to the longitudinal direction.

16. In a device for minimally invasive surgery, the device having an elongated shaft (8) defining a longitudinal direction and adapted to receive an optional additional instrument (7, 7a), an operating handle (6) at a first end of the shaft, and a gripping unit extending from a second end of the shaft; the improvement wherein the gripping unit comprises:

a base section (4) extending to the second end and terminating in a stationary jaw (2) rigidly attached thereto, the base section and the jaw comprising a first channel (9) extending in the longitudinal direction to receive the additional instrument (7, 7a) therein;

a push/pull rod (3) extending to the second end and connected to a movable jaw (1, 1a) via a pin joint (51) having a pin-joint axis; and a coulisse (11a, 11b, 21) whereby the movable jaw (1, 1a) is rotatable generally about a jaw axis generally parallel to the pin-joint axis;

whereby opening and closing of the movable jaw in relation to the stationary jaw is actuatable by a motion of the push/pull rod in the longitudinal direction;

wherein the push/pull rod (3) includes a third channel (30) extending in the longitudinal direction; and wherein the first channel and the third channel together form a circular conduit.

17. The gripping unit according to claim 16, wherein the additional instrument (7, 7a) is insertable from a first end of the shaft into at least one of the first channel, the third channel, the circular conduit (9, 30) and the second channel.

18. The gripping unit according to claim 16, wherein the additional instrument (7, 7a) is rotatable when housed inside the circular conduit.

* * * * *